United States Patent
Kullik et al.

[11] Patent Number: 6,053,031
[45] Date of Patent: Apr. 25, 2000

[54] DETECTION SYSTEM WITH INTERCHANGEABLE SENSORS

[75] Inventors: Götz Kullik; Peter Nink, both of Lübeck, Germany

[73] Assignee: Drägerwerk AG, Germany

[21] Appl. No.: 08/964,258

[22] Filed: Nov. 4, 1997

[30] Foreign Application Priority Data

May 30, 1997 [DE] Germany ............................ 197 22 744

[51] Int. Cl.[7] ............................ G01N 27/416; G01R 1/04
[52] U.S. Cl. ............................ 73/31.05; 73/23.2; 73/866.5
[58] Field of Search ............................ 73/23.2, 31.05, 73/866.5

[56] References Cited

U.S. PATENT DOCUMENTS

| | | | |
|---|---|---|---|
| 4,329,870 | 5/1982 | Farmer | 73/23.2 |
| 4,704,607 | 11/1987 | Teather et al. | 73/1.07 X |
| 4,845,649 | 7/1989 | Eckardt et al. | 702/104 |
| 5,025,653 | 6/1991 | Schuldt | 73/23.2 |
| 5,892,458 | 4/1999 | Anderer et al. | 73/23.2 X |

FOREIGN PATENT DOCUMENTS

| | | | |
|---|---|---|---|
| 0 716 991 | 6/1996 | European Pat. Off. . | |
| 38 19 128 | 10/1995 | Germany | 73/23.2 |
| 2284059 | 5/1995 | United Kingdom | 73/23.2 |

*Primary Examiner*—Daniel S. Larkin
*Attorney, Agent, or Firm*—McGlew and Tuttle, P.C.

[57] ABSTRACT

A detection system with a measuring head, which has a mount for at least one interchangeable sensor, with a component, which is located at the sensor and receives information on the sensor and transmits same to a detection means at the measuring head. Wireless transmission of the sensor information to the measuring head is provided wherein the component is a passive transponder that can be read by supplying external energy in a wireless manner. The transducer includes a data code carrier, in which the sensor information is stored. The detection means has means for supplying the external energy and means for receiving the sensor information.

6 Claims, 2 Drawing Sheets

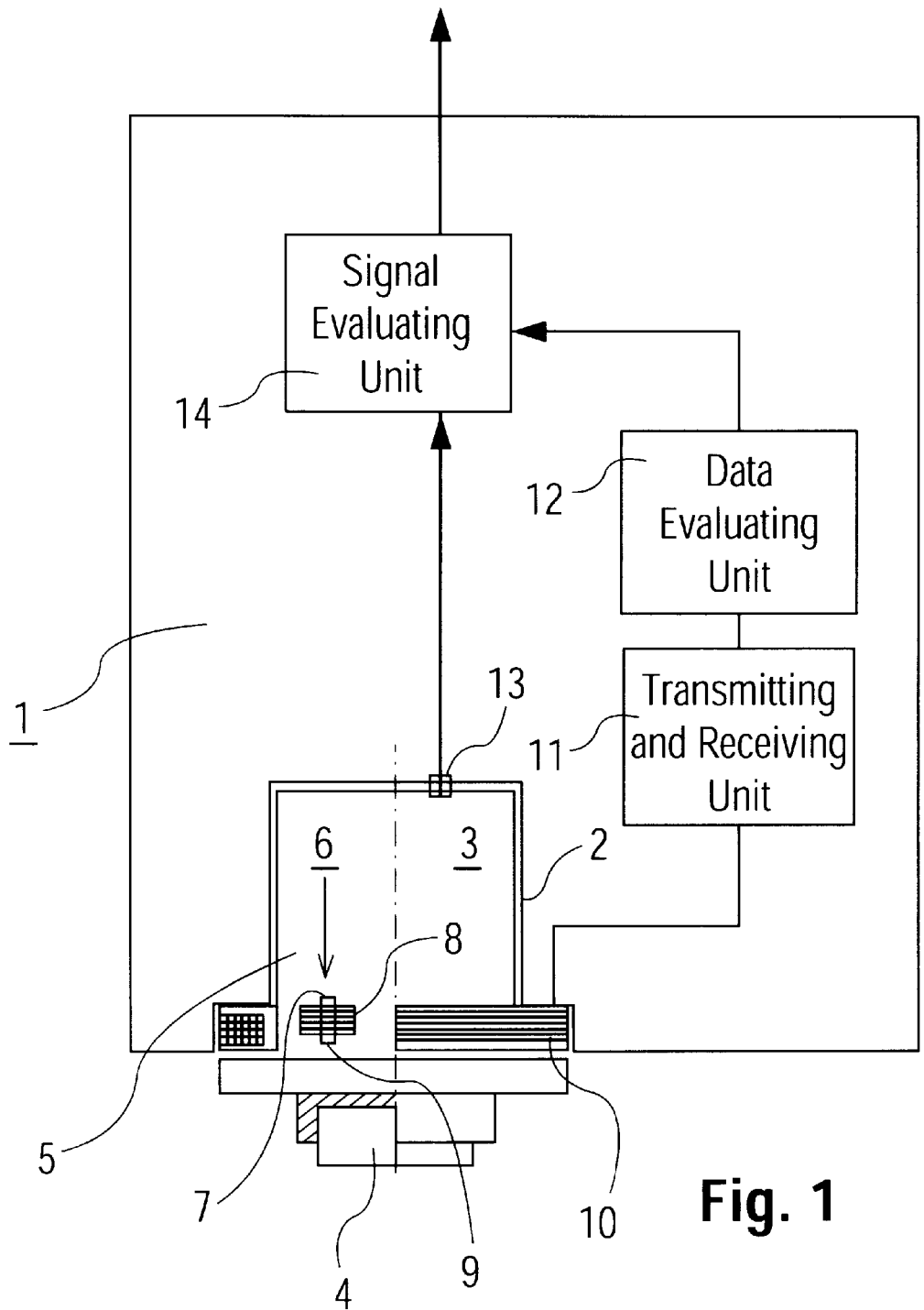

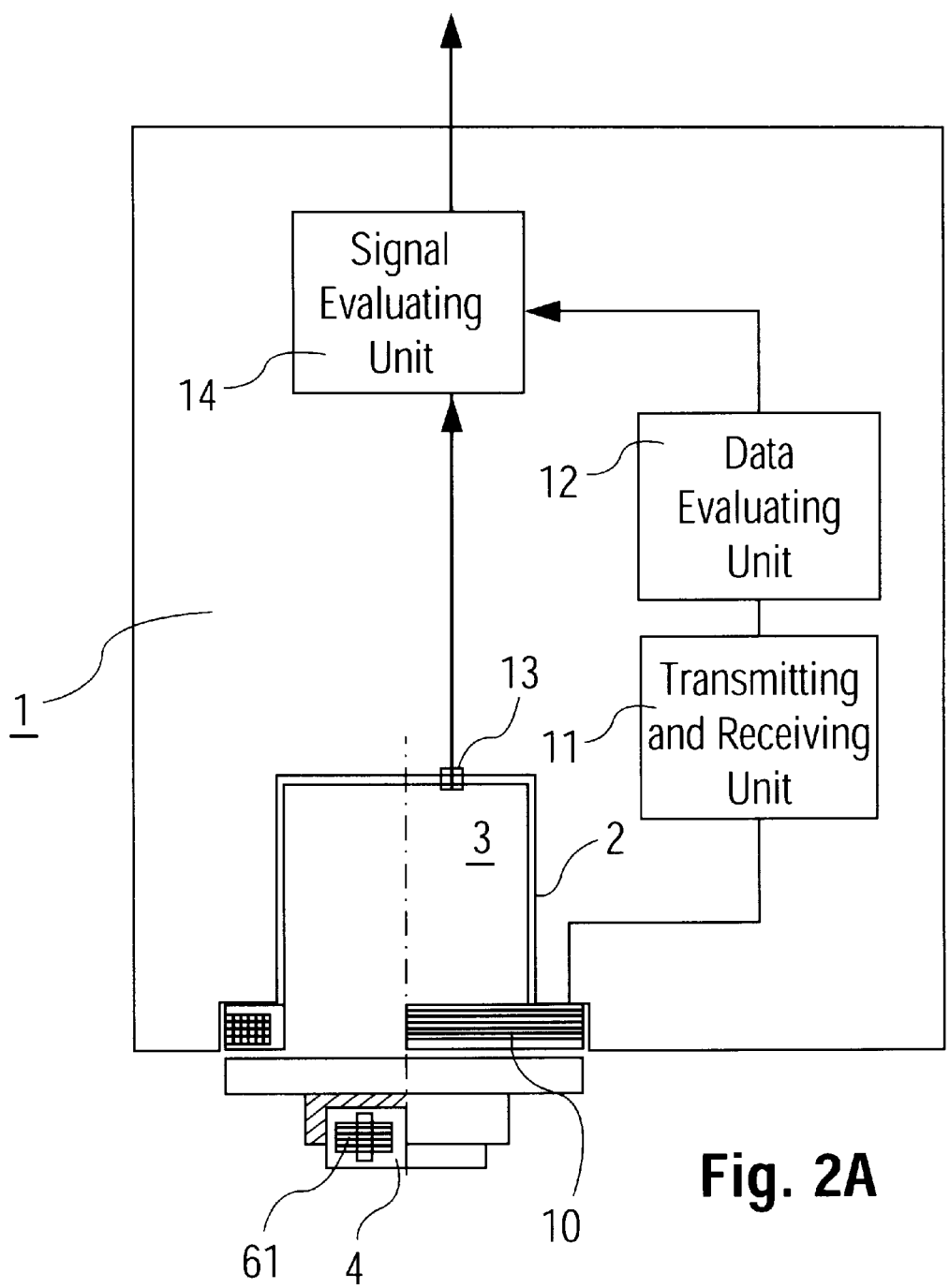

DETECTION SYSTEM WITH INTERCHANGEABLE SENSORS

FIELD OF THE INVENTION

The present invention pertains to a gas detection system with a measuring head, which has a mount for at least one interchangeable sensor, with a component that is located at the sensor and contains information on the sensor and transmits same to a detection means at the measuring head.

BACKGROUND OF THE INVENTION

A gas detection system, which comprises a central unit and a plurality of measuring heads on the site, which are connected to the central unit, has been known from DE 38 19 128 C2. Sensors of various types may be interchangeably inserted in the measuring heads, the sensors being provided in the base area with an identification system in the form of soldered contact bridges, with which the measuring head recognizes the sensor that has been inserted. The prior-art identification system requires a plug in the connection area between the measuring head and the sensor with a plurality of plug contacts to transmit the sensor information to the measuring head in a binary coded form. Such multicontact plugs are expensive, on the one hand, and, on the other hand, the fault liability increases with increasing number of plug contacts. In addition, there is only a limited possibility of retrofitting existing measuring heads for new sensor applications, because the plug coding designed originally must be used for compatibility reasons.

So-called transponder chips with integrated data code carriers, which send a signal to a stationary transmitting and receiving means, have been known from another field of application. The transponder chip contains, besides the data code carrier provided with an individual code, a transmitter and a coil acting as an antenna, wherein the transmitter is supplied with voltage or current from the stationary transmitting and receiving means by inductive coupling. The signal that is sent by the transponder chip from the data code carrier enters the transmitting and receiving means over the same path, but in the opposite direction. Such transponder chips are described in EP 716 991 A1.

SUMMARY AND OBJECTS OF THE INVENTION

The primary object of the present invention is to provide an identification system for sensors, which operates without mechanical coupling between the sensor and the measuring head.

According to the invention, a detection system is provided with a measuring head which has a mount for at least one interchangeable sensor. A component is located at the sensor and contains information on the sensor and transmits this information to a detection means at the measuring head. The component is a passive transponder, which can be read by supplying external energy in a wireless manner, with a data code carrier, in which the information is stored. A detection means is provided with energy supply means for supplying the external energy and sensor receiving means for receiving the sensor information.

The advantage of the present invention is essentially that sensor data can be stored in the data code carrier of a transponder located at the sensor, which data code carrier is designed as an $E^2$-PROM. The data code carrier can be polled by the stationary transmitting and receiving means in the measuring head. By using an $E^2$-PROM as a memory, it is, moreover, also possible to store production data, besides the pure sensor data, e.g., the type of gas and the measuring range, so that it is possible to alert the user to sensors that may no longer be fit for use.

It is especially advantageous for a transponder to be arranged at a component that is detachable from the sensor. Such components may be, e.g., optical or chemical front-sensor filters, which are arranged in front of the measurement system of the sensor.

One advantageous application of passive transponders is to arrange these at sensors of different types, which can be interchangeably inserted in corresponding measuring heads. In a data code carrier, the transponders contain the sensor-specific data, e.g., the type of gas, the measuring range, the date of production, and the name of the manufacturer, which can be transmitted to the evaluating unit of the measuring head in a wireless manner. The transponders are fastened in a suitable area of the housing wall of the sensor. It is useful to use a plurality of transponders in a sensor if it comprises individual components that can be detached from one another and to arrange the transponders at least at some of the detachable components.

One exemplary embodiment of the present invention is shown in the drawing and will be explained in greater detail below.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 1 is a schematic partial sectional and block diagrammatic view of a sensor inserted in a measuring head, with a transponder chip;

FIG. 2A is a schematic partial sectional and block diagrammatic view shows the sensor according to FIG. 1 with a transponder chip arranged in an interchangeable front-sensor filter;

FIG. 2B is a sectional view showing a top of the front-sensor filter of FIG. 2A.

DETAILED DESCRIPTION OF THE PREFERRED EMBODIMENT

Referring to the drawings in particular, FIG. 1 schematically shows a measuring head 1 with a mount 2, into which a gas sensor 3 with a front-sensor filter 4 is inserted. At a housing wall 5, the gas sensor 3 has a chip-like transponder 6, which comprises a transmitter 7, a coil 8 acting as an antenna, and an $E^2$-PROM 9 as a data code carrier for sensor-specific data. An induction coil 10, which is shown in FIG. 1 in a partial sectional view and surrounds the area of the gas sensor 3 provided with the transponder 6 in a ring-shaped pattern, is arranged at the measuring head 1 in the range of action of the transponder. The induction coil 10 is followed by a connected transmitting and receiving unit 11 as well as a sensor data evaluating unit 12. Via a plug-type connection 13 arranged within the mount 2, the measured data determined by the gas sensor 3 are forwarded to a measured signal evaluating unit 14, in which linking with the values furnished by the sensor data evaluating unit 12 is performed.

The mode of action of the device according to the present invention is as follows:

The transponder 6 is supplied with voltage or current from the induction coil 10 fed by the transmitting and receiving unit 11. The induction coil 10 and transmitting and receiving unit 11 form an energy supply means. The sensor-specific data being stored in the $E^2$-PROM 9, such as the type of the sensor, the date of manufacture, and the manufacturer, are transmitted inductively into the transmitting and receiving means 11 via the coil 8 and the induction coil 10, and are intermediately stored in the sensor data evaluating unit 12. The induction coil 10 and transmitting and receiving unit 11 form a sensor information receiving means. The measured signal evaluating unit 14, arranged downstream of the gas sensor 3, and the sensor data evaluating unit 12 contain a microprocessor, not shown in FIG. 1, in which the measured data sent by the gas sensor 3 are first processed with respect to temperature compensation and calibration and are then linked with the sensor-specific data being stored in the sensor data evaluating unit 12. Based on the data read from the sensor data evaluating unit 12, a check is performed in the measured signal evaluating unit 14 to determine whether, e.g., the gas sensor 3 is still fit for use and whether the gas sensor 3 was supplied by an authorized manufacturer. Deviations that may possibly be determined are displayed to the user via a display, not shown in FIG. 1, which is located at the measuring head 1. By using a freely programmable $E^2$-PROM 9 as the data code carrier, it is possible to adapt the structure of the data to be stored to new tasks in a simple manner.

The measuring device illustrated in FIG. 2 differs from the device according to FIG. 1 in that a transponder 61, whose data code carrier, not shown in FIG. 2, is also read by means of the induction coil 10 and the transmitting and receiving unit 11, is arranged at the interchangeable front-sensor filter 4. The transponder 61 has the same design as the transponder 6. Identical components are designated with the same reference numbers as in FIG. 1. The filter data belonging to the front-sensor filter 4 are stored in the $E^2$-PROM of the transponder 61. Via the filter data, which can be polled from the transponder 61, the measured signal evaluating unit 14 obtains information on whether a front-sensor filter 4 is present at all or whether the correct front-sensor filter 4 has been inserted. Confusion, which could lead to a change in the measuring properties of the gas sensor 3, can thus be immediately recognized by means of the filter data being stored in the transponder 61. The lower part of FIG. 2 shows a top view of the front-sensor filter 4.

While specific embodiments of the invention have been shown and described in detail to illustrate the application of the principles of the invention, it will be understood that the invention may be embodied otherwise without departing from such principles.

What is claimed is:

1. A detection system, comprising:

a measuring head with a mount and a detection means;

an interchangeable sensor mounted in said mount;

a passive transponder located adjacent to said sensor, said passive transponder containing information on said sensor and transmitting the information to said detection means at the measuring head, said passive transponder information being read by supplying external energy in a wireless manner, said passive transponder including a data code carrier, in which the information is stored, said detection means including energy supply means for supplying the external energy and sensor information receiving means for receiving the sensor information; and a sensor front-sensor filter that is detachable from said sensor, wherein said transponder is arranged at said front-sensor filter.

2. The detection system in accordance with claim 1, further comprising an additional interchangeable sensor mounted in said mount, said interchangeable sensor and said additional interchangeable sensor being interchangeably inserted into said measuring head.

3. A gas detection method comprising:

providing a measuring head with a mount and a detection means;

providing interchangeable sensors of various types which are mountable in said mount in at least one sensor position, each sensor having a component that is detachable from said sensor said component being a front-sensor filter of said sensor;

providing a passive transponder located adjacent to each of said sensors, and arranged at said component, each of said passive transponders containing information on an associated said sensor filter and transmitting the information to said detection means at the measuring head when said associated sensor is in said at least one sensor position, said passive transponder information being read by supplying external energy in a wireless manner, each of said passive transponders including a data code carrier, in which the information is stored, said detection means including energy supply means for supplying the external energy and sensor information receiving means for receiving the sensor information; and using one or more of said passive transponders at corresponding said sensors of various types, which can be interchangeably inserted into said corresponding measuring head.

4. A gas detection system, comprising:

a measuring head with a mount and a detector;

an interchangeable sensor mounted in said mount;

a passive transponder located adjacent to said sensor, said passive transponder containing information on said sensor and transmitting the information to said detector at the measuring head, said passive transponder information being read by supplying external energy in a wireless manner, said passive transponder including a data code carrier, in which the information is stored, said detector supplying energy and receiving the sensor information;

a component that is detachable from said sensor, wherein said transponder is arranged at said component and wherein said component is a front-sensor filter of said sensor.

5. A gas detection system, comprising:

a measuring head with a mount and a detector;

an interchangeable sensor mounted in said mount;

a component that is detachable from said sensor;

a passive transponder being arranged at said component, said passive transponder containing information of said component and transmitting the information to said detector at the measuring head;

a wireless energy supply device for supplying external energy in a wireless manner to said passive transponder, said information being read by supplying external energy in a wireless manner; and a data code carrier included in said passive transponder, said data code carrier storing information of said component, said detector including said wireless energy supply device and supplying energy and receiving the component information.

6. The gas detection system in accordance with claim 5, wherein said component is a front filter of said sensor and filter data belonging to said front filter are stored in said data code carrier.

* * * * *